United States Patent [19]

Suzuki et al.

[11] 4,334,022
[45] Jun. 8, 1982

[54] METHOD FOR PRODUCING MILDIOMYCIN

[75] Inventors: Takashi Suzuki, Suita; Hidekazu Sawada, Neyagawa; Tsunetomo Asai, Kawanishi, all of Japan

[73] Assignee: Takeda Chemical Industries, Ltd., Osaka, Japan

[21] Appl. No.: 159,925

[22] Filed: Jun. 16, 1980

[30] Foreign Application Priority Data

Jun. 21, 1979 [JP] Japan .................................. 54-78917

[51] Int. Cl.$^3$ ............................................. C12N 1/38
[52] U.S. Cl. .................................... 435/119; 435/244; 435/908
[58] Field of Search ............... 435/119, 908, 128, 886, 435/244, 253; 424/116, 250

[56] References Cited

U.S. PATENT DOCUMENTS 3,926,948  12/1975  Kondo et al. ....................... 435/886
4,007,267   2/1977  Kishi et al. .......................... 435/886

FOREIGN PATENT DOCUMENTS 1507193  4/1978  United Kingdom .

OTHER PUBLICATIONS

Chem. Abs., vol. 84, 1976, 87953u.

Primary Examiner—Hiram Bernstein
Attorney, Agent, or Firm—Wenderoth, Lind & Ponack

[57] ABSTRACT

A method for producing mildiomycin in a commercial quantity and at low cost by cultivating a mildiomycin-producing microorganism belonging to Actinomycetes in a culture medium containing an N-methyl compound in an amount of at least 3 mM to have mildiomycin elaborated and accumulated in the culture broth.

10 Claims, No Drawings

METHOD FOR PRODUCING MILDIOMYCIN

This invention relates to a method for producing mildiomycin. More specifically, this invention is directed to a method for producing mildiomycin by cultivating a mildiomycin-producing microorganism belonging to Actinomycetes in a culture medium to have mildiomycin elaborated and accumulated in the culture broth, characterized in that at least one N-methyl compound is present in the culture medium.

Mildiomycin is an antibiotic substance designated "Antibiotic B-98891" and since it was first discovered, its properties have been studied and its chemical structure determined as being shown below:

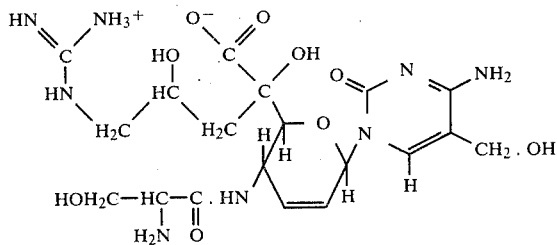

Meanwhile, the present inventors' attention was directed to its activity, particularly its effects as an agent for preventing and treating mildew in a wide variety of plants or as a miticidal agent [U.S. Pat. No. 4,007,267, British Pat. No. 1,507,193 and The Journal of Antibiotics, Vol, 31, No. 6, pages 511–518, 519–524 (1978)].

As a result of vigorous studies made against the background of facts described above, on conditions for the production thereof in order to supply mildiomycin in a commercial quantity and at low cost, the present inventors found that a substantial amount of mildiomycin can be produced in the presence of an N-methyl compound in the culture medium in cultivating an Actinomycetes having an ability to produce mildiomycin and have completed the present invention. Thus, the present invention relates to a method for producing mildiomycin characterized by cultivating a microorganism of Actinomycetes having an ability to produce mildiomycin in a culture medium containing an N-methyl compound in an amount of at least 3 mM to have mildiomycin elaborated and accumulated in the culture broth.

The microorganisms of Actinomycetes having an ability to produce mildiomycin used in the method of this invention includes, for example, Actinomycetes belonging to the genus Streptoverticillium, in particular, *Streptoverticillium rimofaciens* FERM-P 2549 (IFO 13592, ATCC 31120). This organism has been originally identified as *Streptomyces rimofaciens* according to the criteria for classification described in Bergey's Manual of Determinative Bacteriology, 7th Edition [U.S. Pat. No. 4,007,267 and British Pat. No. 1,507,193], but, in view of subsequent modification of criteria for classification, the above microorganism was identified as belonging to the genus Streptoverticillium according to the criteria for classification described in Bergey's Manual of Determinative Bacteriology, 8th Edition (1974) (The Journal of Antibiotics, Vol. 31, No. 6, pages 511–518).

The N-methyl compounds which can be used in the present invention are those having at least one nitrogen atom susbstituted with 1 to 4 methyl groups in the molecule thereof. Of these compounds, those having one nitrogen atom substituted with methyl groups in the molecule thereof are preferred and, in particular, quaternary ammonium salts having trimethylammonio group in which the nitrogen atom is substituted with 3 methyl groups, i.e., $-N^+(CH_3)_3$, are preferred. Further, compounds having a group capable of being converted into a $>N-CH_3$ group in the culture medium, for example, N,N-methylenebisacrylamide, can also be used as said N-methyl compounds. The N-methyl compounds generally have molecular weights in the range of from about 50 to about 1000, preferably 70 to 200, more preferably 90 to 130. The N-methyl compounds may be water-soluble or water-insoluble, but water-soluble N-methyl compounds can be used advantageously. Examples of such N-methyl compounds are N-methyl acid amides, N-methylamino compounds, N-methylamines, N-methylammonium compounds, polymethylenediamines, N,N-methylenebisacrylamide, etc. The N-methyl acid amides such as, for example, N,N-dimethyl $C_{2-6}$ aliphatic acid amides (e.g. N,N-dimethylacetamide, etc.), N-methylalkenylcarbonylamides (e.g. acrylamide, etc.) and the like, the N-methylamino compounds such as, for example, mono, di, tri or tetramethylurea (e.g. N-methylurea, 1,1,3,3-tetramethylurea, etc.), dimethylaminoalcohol (e.g. 2-dimethylaminoethanol, etc.) and the like, the N-methylamines such as, for example, mono, di or trimethylamine (e.g. trimethylamine, dimethylamine, etc.) and the like, the N-methylammonium compounds such as, for example phosphatidylethanol-mono, di or trimethylammonium (e.g. lecithin, etc.), trimethylammonium alcohol (e.g. choline, etc.) trimethylammonium carboxylic acid (e.g. betaine, etc.), alkyltrimethylammonium (e.g. tetramethylammonium, etc.), ethylenebis(trimethylammonium)chloride and the like, and polymethylenediamines such as, for example, ethylenediamine, tetramethylenediamine, hexamethylenediamine and the like can be used advantageously. A satisfactory result can be obtained with N-methylammonium compounds, particularly choline, betaine or tetramethylammonium. These N-methyl compounds can be used alone or as a mixture of two or more species. The present invention also includes, within the scope thereof, a method comprising adding a large amount of an N-methyl compound-containing substance, for example, beat molasses containing betaine, soybean meal containing lecithin or hen's egg containing both choline and lecithin, etc. to a culture medium so as to provide more than 3 mM of N-methyl compounds to the medium. The concentration of N-methyl compound in the culture medium can be suitably selected from within the range which does not inhibit growth of the microorganism used and is adjusted to more than 3 mM. The concentration is preferably 4 mM to 200 mM, more preferably 7 to 50 mM and, at a higher concentration exceeding 200 mM, the effect achieved by addition of N-methyl compounds tends to be not so remarkable as compared with the effect obtained below 200 mM. The amount of naturally-occurring substances containing N-methyl compounds can be selected so as to provide the N-methyl compound concentration as specified above, but such concentration would require a larger amount of naturally-occurring substances than that conventionally used whereby the growth of microorganism may be adversely affected by components of the naturally-occurring substances other than N-methyl compounds thereby preventing the production of mildiomycin. In such cases, it is preferred to use N-methyl compounds in combination with the naturally-occurring substances. The time at which the N-methyl compound is incorporated in the culture medium is preferably before the culture medium is inoculated with the microorganism in view of ease in operation and effectiveness, but the N-methyl compound can also be added at an appropriate time during the cultivation.

The carbon sources which can be used in the culture medium for cultivation include sugars which can be utilized by the microorganism used, for example, starch, dextrin, glucose, maltose, sucrose, sorbitol as well as molasses, corn syrup, millet jelly, etc., and organic acids such as acetic acid, succinic acid and the like and fats and oils. The nitrogen sources which can be used are various ammonium salts, nitrates, urea as well as organic naturally-occurring substances such as yeast extract, casein, meat extract, cottonseed flour, corn steep liquor, soybean meal and the like. The medium may further as an inorganic salt contain salts of iron, magnesium, manganese, cobalt, copper, sodium, potassium, calcium, zinc, etc., if necessary. Further, the medium may suitably contain specific nutrients such as amino acids, vitamins, purine- and pyrimidine-bases and the like, if the microorganism requires such nutrients.

The cultivation can be conducted by any of stationary, submerged aerobic, shake and other cultured methods, but generally submerged aerobic culture is preferred. The cultivation temperature can be from 20° C. to 40° C., preferably from 24° C. to 34° C. The culture medium is preferably maintained at a pH in the range from 4 to 9 and, for this purpose, the pH value of the medium is adjusted with a dilute aqueous solution of caustic alkali or aqueous ammonium or a dilute aqueous solution of sulfuric acid, hydrochloric acid or the like during the cultivation. Alkali salts such as potassium carbonate, sodium carbonate, etc. can also be added to the medium. The method of the present invention can be practiced by continuing the cultivation until a substantial amount of mildiomycin is elaborated and accumulated in the culture broth and generally the maximum yield of mildiomycin can be obtained in 4 to 12 days.

From the culture broth obtained in the above manner, mildiomycin can be isolated, if necessary, by conventional procedures which are normally utilized for the recovery of basic water-soluble antibiotics. For example, after the microbial cells and other insoluble matter in the culture broth are removed by a procedure such as filtration, centrifugation or the like, the filtrate or supernatant is contacted with activated carbon or adsorptive resins to absorb mildiomycin and, thereafter, mildiomycin can be eluted with an aqueous organic solvent, an aqueous salt or acid solution, a buffer solution or the like. Since the antibiotic produced in accordance with the present invention is a basic substance, it is adsorbed well on a cation-exchange resin and can be eluted with a suitable acid, alkali or buffer solution. Such procedures can be suitably used selectively and in combination and thereafter the eluate is concentrated and crystallized to obtain mildiomycin. Mildiomycin thus obtained can be used safely as an active ingredient of an antibacterial and miticidal agent for plants as described in U.S. Pat. No. 4,007,267 and British Pat. No. 1,507,193.

The present invention is further illustrated in greater detail by the following Examples, it being understood that these examples are not to be construed as limiting the present invention. In this specification, the following abbreviations are used: milliliter=ml, liter=l, gram=g, percent (weight/volume)=%, nano meter=nm, rotation per minutes=r.p.m. The numbers indicated by IFO, FERM-P and ATCC are the accession numbers at Institute for Fermentation, OSAKA, JAPAN; the Fermentation Research Institute of the Agency of Industrial Science and Technology, Chiba, JAPAN; and American Type Culture Collection, U.S.A., respectively.

EXAMPLE 1

(1) To 25 ml of a culture medium comprising 10% glucose, 3% cottonseed flour (trade name; Proflo, Trader Oil Mill Co., U.S.A.), 1% corn steep liquor, 0.5% sodium chloride, 0.001% ferrous sulfate and 0.5% calcium carbonate was added choline at a concentration indicated below in Table 1, and a 20% aqueous sodium hydroxide solution was added dropwise to the mixture to adjust the pH value of 7.0. The medium was then sterilized and inoculated with one platinum loop of a slant culture of *Streptoverticillium rimofaciens* FERM-P 2549 (IFO 13592, ATCC 31120), followed by cultivation on a rotatory shaker at 200 r.p.m. and at 28° C. for 120 hours. Quantitative assay of the culture broth for mildiomycin according to the known procedure reported in The Journal of Antibiotics, Vol. 31, No. 6, pages 511–518 and 519–524 (1978) gave the results shown in Table 1.

TABLE 1

| Amount of choline Added (mM) | Relative Titer of mildiomycin (weight ratio) |
|---|---|
| 0 | 100 |
| 0.35 | 113 |
| 1.40 | 133 |
| 3.5 | 180 |
| 14.0 | 193 |
| 35.0 | 200 |
| 70.0 | 200 |

(2) 1 l of the culture broth obtained in (1) above using the culture medium to which choline was added at a concentration of 14 mM was collected and centrifuged to obtain a supernatant which was then passed through a column packed with 500 ml of an ion-exchange resin Amberlite IRC-50 (H+ form) (Rohm & Haas Co., U.S.A.). The column was washed with water and, thereafter, elution was performed using 500 ml of 0.5% aqueous ammonia. The active fractions were adsorbed by passing through a column packed with 50 ml of activated carbon for chromatography (manufactured by Takeda Chemical Industries, Ltd., Japan). The active fractions eluted with 250 ml of a solvent mixture of acetone and water (3:7) were collected and concentrated, and acetone was added dropwise to the concentrate to precipitate crude mildiomycin. The crude powder (1.3 g) thus obtained was dissolved in water and the solution was passed through a column of 25 ml of Amberlite CG-50 (H+ form) (Rohm & Haas Co., U.S.A.). The column was washed with 10 ml of water and elution was then carried out with 250 ml of 0.5% aqueous ammonia. The active fractions were collected and adsorbed by passing through a column of 50 ml of activated carbon. Fractional elution was performed using 250 ml of acetone-0.1 N formic acid (2:8) and the active fractions were concentrated. Methanol was added to the concentrate to precipitate mildiomycin. The resulting precipitate was dried under reduced pressure to obtain 1.1 g of mildiomycin formate. Of their physical and chemical properties, the melting point, the optical rotation ($[\alpha]_D^{24}$ at c, 1.0 in $H_2O$ and c, 1.0 in 0.1—N HCl) and the ultraviolet absorbance indexes at 271 nm and 280 nm were found to be highly consistent with those reported in the literature (The Journal of Antibiotics, Vol. 31, No. 6, p. 523, 1978).

EXAMPLE 2

The cultivation of the mildiomycin-producing microorganism was conducted in the same manner as described in Example 1 except that each of the various N-methyl compounds shown below in Table 2 was added to the culture medium at a concentration of 7 mM in place of 14 mM of choline. The results obtained by quantitative mildiomycin assay are shown in Table 2.

TABLE 2

| Additive (7 mM) | Relative Titer of mildiomycin (weight ratio) |
| --- | --- |
| No addition | 100 |
| Choline | 187 |
| Betaine | 186 |
| Lecithin | 161 |
| Trimethylamine | 175 |
| Tetramethylammonium | 187 |
| N,N-Methylenebisacrylamide | 170 |

EXAMPLE 3

The cultivation was conducted in the same manner as described in Example 1 except that betaine was added to the culture medium in place of choline at the various concentrations shown below in Table 3. The results obtained by quantitative mildiomycin assay are shown in Table 3.

TABLE 3

| Amount of Betaine Added (mM) | Relative Titer of mildiomycin (weight ratio) |
| --- | --- |
| No addition | 100 |
| 0.35 | 110 |
| 1.40 | 129 |
| 3.5 | 160 |
| 14.0 | 185 |
| 35.0 | 194 |
| 70.0 | 200 |

EXAMPLE 4

The cultivation was conducted in the same manner as described in Example 1 except that choline and tetramethylammonium hydrochloride, in various combinations, were added to the culture medium in place of choline at the concentrations shown below in Table 4. The results obtained by quantitative mildiomycin assay are shown in Table 4.

TABLE 4

| Amount of Choline Added (mM) | Amount of Tetramethyl-ammonium Hydrochloride Added (mM) | Relative Titer of mildiomycin (weight ratio) |
| --- | --- | --- |
| No addition | No addition | 100 |
| 7 | 0 | 187 |
| 6 | 1 | 187 |
| 5 | 2 | 185 |
| 4 | 3 | 186 |
| 3 | 4 | 188 |
| 2 | 5 | 187 |
| 1 | 6 | 188 |
| 0 | 7 | 187 |

EXAMPLE 5

The cultivation was conducted in the same manner as described in Example 1 except that 1,1,3,3-tetramethylurea was added to the culture medium in place of choline and the timing of addition was varied as indicated in Table 5. The results obtained by quantitative mildiomycin assay are shown in Table 5.

TABLE 5

| Cultivation Time at which 1,1,3,3-Tetramethylurea is added (Hour) | Relative Titer of mildiomycin (weight ratio) |
| --- | --- |
| 0 | 140 |
| 10 | 140 |
| (No addition) | 100 |

What we claim is:

1. In a method for producing mildiomycin which comprises cultivating a mildiomycin-producing microorganism belonging to the genus Streptoverticillium in a culture medium to elaborate and accumulate mildiomycin in the culture broth, the improvement wherein the cultivation is carried out in the presence of an N-methyl compound and wherein the concentration of N-methyl compound in the culture medium is at least 3 mM.

2. A method according to claim 1, wherein the N-methyl compound has at least one nitrogen atom substituted with 1 to 4 methyl groups in the molecule thereof.

3. A method according to claim 1, wherein the N-methyl compound is selected from the group consisting of N-methyl acid amides, N-methylamino compounds, N-methylamines, N-methylammonium compounds and compounds having a group capable of being converted into a >N—CH$_3$ group in the culture medium, said N-methyl compound having molecular weight in the range of from 50 to 1000.

4. A method according to claim 3, wherein the N-methyl compound has molecular weight in the range of from 90 to 130.

5. A method according to claim 1, wherein the N-methyl compound is selected from the group consisting of N-methylamines, N-methylammonium compounds and compounds having a group capable of being converted into a >N—CH$_3$ group in the culture medium, said N-methyl compound having molecular weight in the range of from 50 to 1000.

6. A method according to claim 5, wherein the N-methyl compound is a member selected from the group consisting of trimethylamine, lecithin, choline, betaine and tetramethylammonium.

7. A method according to claim 1, wherein the N-methyl compound is a N-methylammonium compound having trimethylammonino group and molecular weight in the range of from 70 to 200.

8. A method according to claim 7, wherein the N-methylammonium compound is choline.

9. A method according to claim 1, wherein a concentration of N-methyl compound in the culture medium is 4 to 200 mM.

10. A method according to claim 1, wherein the concentration is 7 to 50 mM.

* * * * *